United States Patent [19]

Misch

[11] Patent Number: 4,500,292
[45] Date of Patent: Feb. 19, 1985

[54] METHOD AND APPARATUS FOR PREPARING MUCOSAL TISSUE FOR THE RECEPTION OF DENTURE ANCHORING INTRAMUCOSAL INSERTS

[76] Inventor: Carl E. Misch, 1611 Monroe, Dearborn, Mich. 48124

[21] Appl. No.: 517,569

[22] Filed: Jul. 27, 1983

[51] Int. Cl.³ .............................................. A01C 8/00
[52] U.S. Cl. .................................................... 433/173
[58] Field of Search ................ 433/173, 174, 175, 176

[56] References Cited

U.S. PATENT DOCUMENTS

| 2,112,007 | 3/1938 | Adams | 433/174 |
| 2,374,422 | 4/1945 | Dahl | 433/173 |
| 2,857,670 | 10/1958 | Kiernan | 433/175 |

*Primary Examiner*—Robert Peshock
*Attorney, Agent, or Firm*—Basile, Weintraub & Hanlon

[57] ABSTRACT

A method for preparing the mucosal tissue of a patient for the reception of a denture anchoring intramucosal insert employs a temporary insert of a construction such that it may be inserted into a freshly formed cavity in the mucosal tissue during the healing period without interfering with usage of a normal denture.

3 Claims, 5 Drawing Figures 4,500,292

METHOD AND APPARATUS FOR PREPARING MUCOSAL TISSUE FOR THE RECEPTION OF DENTURE ANCHORING INTRAMUCOSAL INSERTS

BACKGROUND OF THE INVENTION

The use of intramucosal inserts for anchoring or retaining dentures in place is well known. This technique is used in those cases where, for any of several common reasons, the contact between the denture and the patient's mucosal tissue cannot, by itself, adequately hold the denture in the desired position.

In practicing this technique the dentist forms, by drilling, a series of cavities in the patient's mucosal tissue. Inserts in the form of an enlarged head mounted at the distal end of a shaft are fixedly mounted on the interior surface of the denture to be received within the cavities formed in the mucosal tissue, thus anchoring the denture in place. Examples of intramucosal inserts are shown and described in my U.S. Pat. No. 4,382,791 and Weiss et al, U.S. Pat. No. 3,905,108.

As stated above, the insert-receiving cavity is formed in the patient's mucosal tissue by a drilling operation and there is, of necessity, an initial healing period. Weiss et al, supra, states that the healing period is six to eight weeks, during which regeneration of the mucosal tissue approximately conforms the shape of the cavity to that of the insert. Most inserts are of what might best be described as a "mushroom-type" shape which requires a fair amount of tissue regeneration before adequate retention is achieved. Thus, until the healing process has had a chance to develop at least some tissue regeneration, the original problems of slippage and movement of the denture still remain. This, in turn, prolongs the healing process and is a source of extreme pain, discomfort and aggravation to the patient.

The present invention provides a solution to this last problem.

SUMMARY OF THE PRESENT INVENTION

In accordance with the present invention, a temporary insert, of a similar size and shape as the exposed portions of the permanent insert attached to the denture, is employed and is inserted in the mucosal cavity during the healing period. The temporary insert has an enlarged head and projecting shaft of a similar size and shape of that portion of the permanent insert which projects from the denture. A thin retaining plate is secured to that end of the shaft of the temporary insert remote from the enlarged head and is in the form of a disc which projects radially from the shaft. This retainer plate is seated flush against the surface of the mucosal tissue when the temporary insert is seated within the cavity and effectively establishes an end limit to inward movement of the insert into the cavity as well as providing a convenient means for withdrawing the temporary insert from the cavity. The thickness of the retainer plate is, however, insufficient to provide any substantial interference with a normal denture which may be used by the patient while the healing process is taking place. Slippage or movement of the normal denture does not cause any substantial movement of the temporary insert.

Other objects and features of the invention will become apparent by reference to the following specification and to the drawings.

DETAILED DESCRIPTION OF THE PREFERRED EMBODIMENTS

Figure 1:
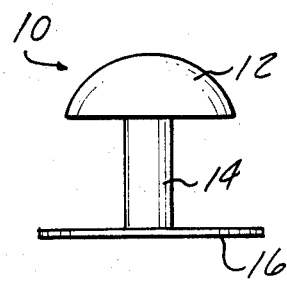
FIG. 1 is a side-elevational view of a temporary insert embodying the present invention.
Figure 2:
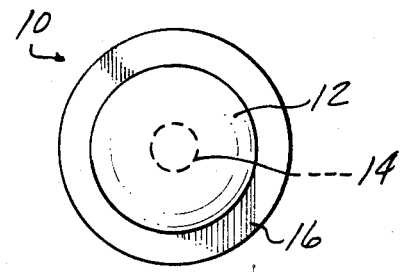
FIG. 2 is a top-plan view of the insert of FIG. 1.
Figure 3:
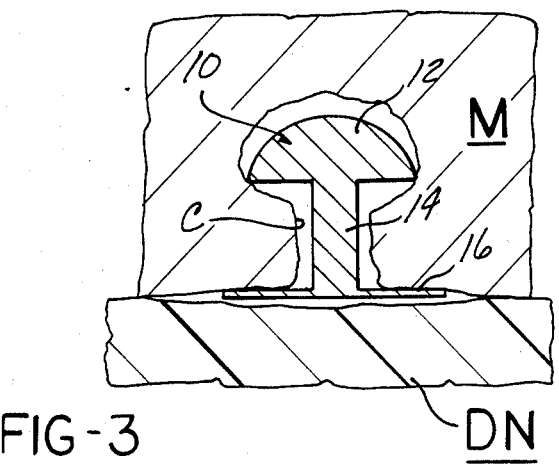
FIG. 3 is a cross-sectional view of the temporary insert installed in a cavity in the mucosal tissue of a patient.

A temporary intramucosal insert embodying the present invention is shown in FIGS. 1, 2 and 3 of the drawings. The temporary insert designated, generally, at 10 includes an enlarged mushroom-shaped head 12 which is fixedly mounted at one end of a stem or shaft 14. At the opposite end of shaft 14, a relatively thin disk-shaped retainer plate 16 is fixedly secured to shaft 14.

Figure 1A:
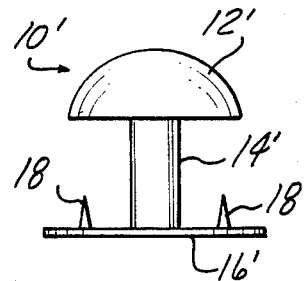
FIG. 1a is a modified form of the insert of FIG. 1.

A slightly modified form of insert 10' is shown in FIG. 1a which includes a head 12', shaft 14' and plate 16' identical to elements 12, 14 and 16. In the FIG. 1a embodiment, pins 18 are fixedly mounted upon and project from the side of plate 16' which faces head 12'.

Figure 4:
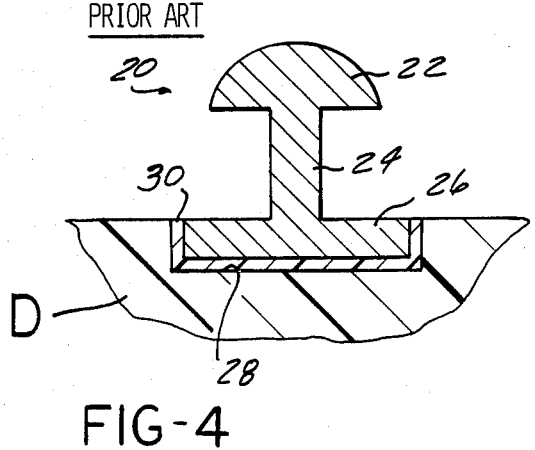
FIG. 4 is a cross-sectional view of a portion of a denture with a permanent intramucosal insert installed in accordance with prior art teachings.

Referring now to FIG. 4, there is shown a portion of a denture designated generally D upon which is installed a prior art permanent intramucosal insert designated generally 20 of the type disclosed in my prior U.S. Pat. No. 4,382,791. The permanent insert 20 includes a mushroom-shaped head 22 integrally formed upon one end of a central shaft 24 whose opposite end is in turn integral with a relatively thick base 26. Base 26 of the permanent insert 20 is fixedly secured within a recess 28 formed in denture D by a suitable adhesive 30, as described in my U.S. Pat. No. 4,382,791.

It should be noted with respect hereto that the temporary insert hereof differs from that in my previous patent, U.S. Pat. No. 4,382,791, in the thickness and structure of plate 16. Herein, plate 16 is devoid of the peripheral grooves because there is no need for them. Likewise, the plate 16 is thinner than the plate of the permanent insert. The plate 16 hereof is of a thickness insufficient to attach a denture to it.

In the practice of the present invention, the size and shape of the enlarged head 12 and shaft 14 of the temporary insert 10 are made identical to the enlarged head 22 and shaft 24 of the permanent insert 20 which is to be installed on a patient's denture.

PROCEDURE

Insert receiving cavities C (FIG. 3) are formed in the mucosal tissue M of the patient by a drilling operation in the conventional manner. As initially formed, this cavity C is essentially a bore whose bottom is enlarged in the manner described in my U.S. Pat. No. 4,382,791.

In accordance with prior art practice, after the necessary number of cavities C were formed in the patients mucosal tissue, a denture with appropriately located permanent inserts 20 was put in place by forcing the permanent inserts into the freshly formed cavities C. Until the healing process had progressed to a point where mucosal tissue regeneration began to closely conform to the shape of the insert, the "grip" of the mucosal tissue on the various inserts was not particularly firm and thus some movement or slipping of the denture relative to the patients gum would occur. In addition to being painful and frustrating to the patient, this slippage or movement of the denture interfered with the healing process and regeneration of the mucosal tissue.

In contrast in accordance with the present invention the cavities C in the patients mucosal tissue are formed a week or more before the patient first uses a denture with permanently installed intramucosal inserts.

In the practice of the present invention immediately after the formation of the cavities C in the patients mucosal tissue, temporary inserts 10 are seated in the cavities with the retainer plate portion 16 of the inserts located flush against the gum surface as indicated in FIG. 3. The patients normal insertless denture DN is then placed in position and used by the patient over the healing period. In those cases where it is desired to firmly hold the temporary insert in position, an insert 10' of the form shown in FIG. 1a is used, the pieces 18 seating themselves in the mucosal tissue.

Because the normal denture DN is not attached in any manner to the temporary insert 10, and the retainer plate portion 16 of temporary insert 10 is thin enough so that it does not substantially interfere with the seating of denture DN, slippage or movement of the denture DN relative to the gum is not transmitted to the installed temporary insert 10. This not only minimizes pain, but also permits a much more rapid healing process than occurs in the prior art procedure described above.

When the healing process has reached a satisfactory stage, which in some cases takes as little as one week, the temporary inserts are removed and the normal denture DN is replaced with a denture D having permanently mounted inserts of the type shown in FIG. 4.

While one embodiment of the invention has been disclosed in detail, it will be apparent to those skilled in the art that the disclosed embodiment may be modified. Therefore, the foregoing description is to be considered exemplary rather than limiting, and the true scope of the invention is that defined in the following claims.

What is claimed is:

1. A temporary insert for use in preparing a freshly formed cavity in the mucosal tissue of a patient for the reception of an intramucosal insert permanently attached to a denture, said intramucosal insert having a shaft with an enlarged head fixedly secured to and projecting from the inner surface of the denture, said temporary insert comprising:
   a shaft formed with an enlarged head at one end thereof of a size and shape the same as that of the shaft and enlarged head of said intramucosal insert, said head having a dome-like face opposed to the shaft and a flat, planar face contiguous to the shaft adjoining the upper at an angle; and
   a thin retainer plate fixedly secured to the other end of said shaft of said temporary insert to lie flat against the surface of mucosal tissue of a patient when the shaft and head of said temporary insert are seated within said freshly formed cavity;
   the thickness of said plate being insufficient to exert any substantial interference with a normal denture seated on said mucosal tissue in unattached overlying relationship to said temporary insert when said temporary insert is seated in said cavity.

2. A temporary insert for use in preparing a freshly formed cavity in the mucosal tissue of a patent for the reception of an intramucosal insert permanently attached to a denture, said intramucosal insert having a shaft with an enlarged head fixedly secured to and projecting from the inner surface of the denture, said temporary insert comprising:
   a shaft formed with an enlarged head at one end thereof of a size and shape the same as that of the shaft and enlarged head of said intramucosal insert;
   a thin retainer plate fixedly secured to the other end of said shaft of said temporary insert to lie flat against the surface of mucosal tissue of a patient when the shaft and head of said temporary insert are seated within said freshly formed cavity;
   the thickness of said plate being insufficient to exert any substantial interference with a normal denture seated on said mucosal tissue in unattached overlying relationship to said temporary insert when said temporary insert is seated in said cavity; and
   a plurality of mucosal penetrating pins mounted upon and projecting from the side of said retaining plate facing the head.

3. A method for preparing the mucosal tissue of a patient for the reception of denture anchoring intramucosal inserts comprising the steps of:
   1. forming appropriately located cavities in the mucosal tissue,
   2. inserting into each of the freshly formed cavities a temporary insert conformed to that portion of the denture anchoring insert to be received and locating a thin retaining plate attached to the temporary insert in substantially flush face to face engagement with the surface of the mucosal tissue adjacent the cavity,
   3. placing a normal insertless denture on the mucosal tissue in overlying relationship to the inserted temporary inserts for normal usage by the patient until the cavities are at least partially healed; and
   4. removing the temporary inserts from the partially healed cavities for subsequent insertion of a denture bearing permanently attached projections into the prepared cavities for permanently attaching the denture to the mucosal tissue of the user.

* * * * *